United States Patent
Brunner et al.

(10) Patent No.: US 7,734,009 B2
(45) Date of Patent: Jun. 8, 2010

(54) ANGIOGRAPHIC X-RAY DIAGNOSTIC DEVICE FOR ROTATION ANGIOGRAPHY

(75) Inventors: Thomas Brunner, Nürnberg (DE); Klaus Klingenbeck-Regn, Nürnberg (DE); Michael Maschke, Lonnerstadt (DE); Alois Nöttling, Pottenstein (DE); Ernst-Peter Rührnschopf, Erlangen (DE); Bernhard Scholz, Heroldsbach (DE); Bernd Schreiber, Heroldsbach (DE); Norbert Karl Strobel, Palo Alto, CA (US); Karl Wiesent, Erlangen (DE); Michael Zellerhoff, Forchhelm (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/284,235

(22) Filed: Nov. 21, 2005

(65) Prior Publication Data

US 2006/0120507 A1 Jun. 8, 2006

(30) Foreign Application Priority Data

Nov. 26, 2004 (DE) .................. 10 2004 057 308

(51) Int. Cl.
*G01N 23/083* (2006.01)
*H05G 1/02* (2006.01)
(52) U.S. Cl. .................. 378/62; 378/15; 378/210
(58) Field of Classification Search .......... 378/4–9, 378/15, 62, 210
See application file for complete search history.

(56) References Cited

U.S. PATENT DOCUMENTS

| | | | |
|---|---|---|---|
| 5,630,414 A | * | 5/1997 | Horbaschek ............. 600/428 |
| 5,646,525 A | | 7/1997 | Gilboa |
| 5,666,391 A | | 9/1997 | Ohnesorge et al. |
| 5,764,719 A | | 6/1998 | Noettling |
| 5,852,646 A | * | 12/1998 | Klotz et al. ............. 378/8 |
| 6,041,097 A | * | 3/2000 | Roos et al. ............. 378/62 |
| 6,173,033 B1 | | 1/2001 | Klingenbeck-Regn et al. |

(Continued)

FOREIGN PATENT DOCUMENTS

CN 1207888 A 2/1999

(Continued)

OTHER PUBLICATIONS

E. Euler, S. Heining, T. Fischer, K. J. Pfeifer, W. Mutschler; "Initial Clinical Experiences with the SIREMOBIL Iso-C$^{3D}$"; Electromedia 70 (2002); pp. 48-51; No. 1.

(Continued)

*Primary Examiner*—Edward J Glick
*Assistant Examiner*—Anastasia Midkiff

(57) ABSTRACT

The invention relates to an angiographic x-ray diagnostic device for rotation angiography with an x-ray emitter which can be moved on a circular path about a patient located on a patient support table, with an image detector unit which can moved on the circular path facing the x-ray emitter, with a digital image system for recording a plurality of projection images by means of rotation angiography, with a device for image processing, by means of which the projection images are reconstructed into a 3D volume image, and with a device for correcting physical effects and/or inadequacies in the recording system such as truncation correction, scatter correction, ring artifact correction, correction of the beam hardening and/or of the low frequency drop for the soft tissue display of projection images and the 3D volume images resulting therefrom.

11 Claims, 2 Drawing Sheets

U.S. PATENT DOCUMENTS

| | | | |
|---|---|---|---|
| 6,233,476 | B1 | 5/2001 | Strommer et al. |
| 6,236,705 | B1 | 5/2001 | Stergiopoulos et al. |
| 6,379,041 | B1 | 4/2002 | Schuetz et al. |
| 6,650,724 | B2 | 11/2003 | Strobel |
| 6,788,759 | B2 * | 9/2004 | Op De Beek et al. ......... 378/19 |
| 6,842,502 | B2 * | 1/2005 | Jaffray et al. ................ 378/65 |
| 7,020,235 | B2 | 3/2006 | Hornegger et al. |
| 7,308,072 | B2 * | 12/2007 | Ruhrnschopf .................. 378/7 |
| 2001/0031919 | A1 | 10/2001 | Strommer et al. |
| 2002/0071101 | A1 | 6/2002 | Horbaschek et al. |
| 2003/0031299 | A1 * | 2/2003 | Ohishi ........................ 378/162 |
| 2004/0008882 | A1 | 1/2004 | Hornegger et al. |
| 2004/0066906 | A1 | 4/2004 | Hornegger et al. |
| 2006/0008046 | A1 | 1/2006 | Ruhrnschopf |
| 2006/0115054 | A1 * | 6/2006 | Yatsenko et al. ............ 378/207 |

FOREIGN PATENT DOCUMENTS

| | | | |
|---|---|---|---|
| CN | 1213280 A | | 3/2001 |
| DE | 195 09 007 C2 | | 9/1996 |
| DE | 199 50 793 B4 | | 8/2000 |
| DE | 100 36 143 C2 | | 2/2002 |
| DE | 100 47 364 A1 | | 4/2002 |
| DE | 101 22 875 C1 | | 2/2003 |
| DE | 102 24 011 A1 | | 12/2003 |
| DE | 102 41 184 A1 | | 4/2004 |
| DE | 103 06 068 A1 | | 6/2004 |
| DE | 10 2004 029 009 A1 | | 1/2006 |
| WO | 9733518 A1 | | 9/1997 |

OTHER PUBLICATIONS

Jared Starman, Norbert Strobel, Norbert Pelc, Rebecca Fahrig, "Extrapolating Truncated Projections Using $0^{th}$ and $1^{st}$ Moment Constraints", RSNA, Nov. 28, 2004, pp. 1-4, Retrieved from Internet Apr. 19, 2004, http://rsna2004.rsna.org/rsna2004/004/conference/event_display.cfm?em_id=4415937.

Krishnakumar Ramamurthi and Jerry Prince, "Tomographic Reconstruction for Truncated Cone Beam Data Using Prior CT Information", Lecture notes in Computer Science, 2003, pp. 134-141, vol. 2879, Springer-Verlag Berlin Heidelberg, ISBN# 3-540-20464-4.

Alexander Katsevich, "A General Scheme for Constructing Inversion Algorithms for Cone Beam CT", 2003, pp. 1305-321, vol. 2003, Issue 21, Hindawi Publishing Corp.

Ruola Ning, Xiangyang Tang and David L. Conover, "X-Ray Scatter Suppression Algorithm for Cone Beam Volume CT", Proceedings of SPIE, Medical Imaging 2002: Physics of Medical Imaging, May 2002, pp. 774-781, vol. 4682.

Karl Wiesent, K. Barth, N. Navab, P. Durlak, T. Brunner, O. Schuetz, W. Seissler, "Enhanced 3-D-Reconstruction Algorithm for C-Arm Systems Suitable for Interventional Procedures", IEEE Transactions on Medical Imaging, May 2000, pp. 391-403, vol. 19, No. 5.

B. Ohnesorge, T. Flohr, K. Schwarz, J.P. Heiken, K.T. Bae, "Efficient Correction for CT Image Artifacts Caused by Objects Extending Outside the Scan Field of View", Med. Phys. 27, Jan. 2000, pp. 39-46, vol. 1.

L.A. Feldkamp, L.C. Davis, J.W. Kress, "Practical Con-Beam Algorithm", J. Opt. Soc. Am. A, Jun. 1984, pp. 612-619, vol. 1, No. 6.

Harrison H. Barrett, William Swindell, "Radiological Imaging, The Theory of Image Formation, Detection and Processing", 1981, pp. 375-464, vol. 2, Academic Press, Inc.

* cited by examiner

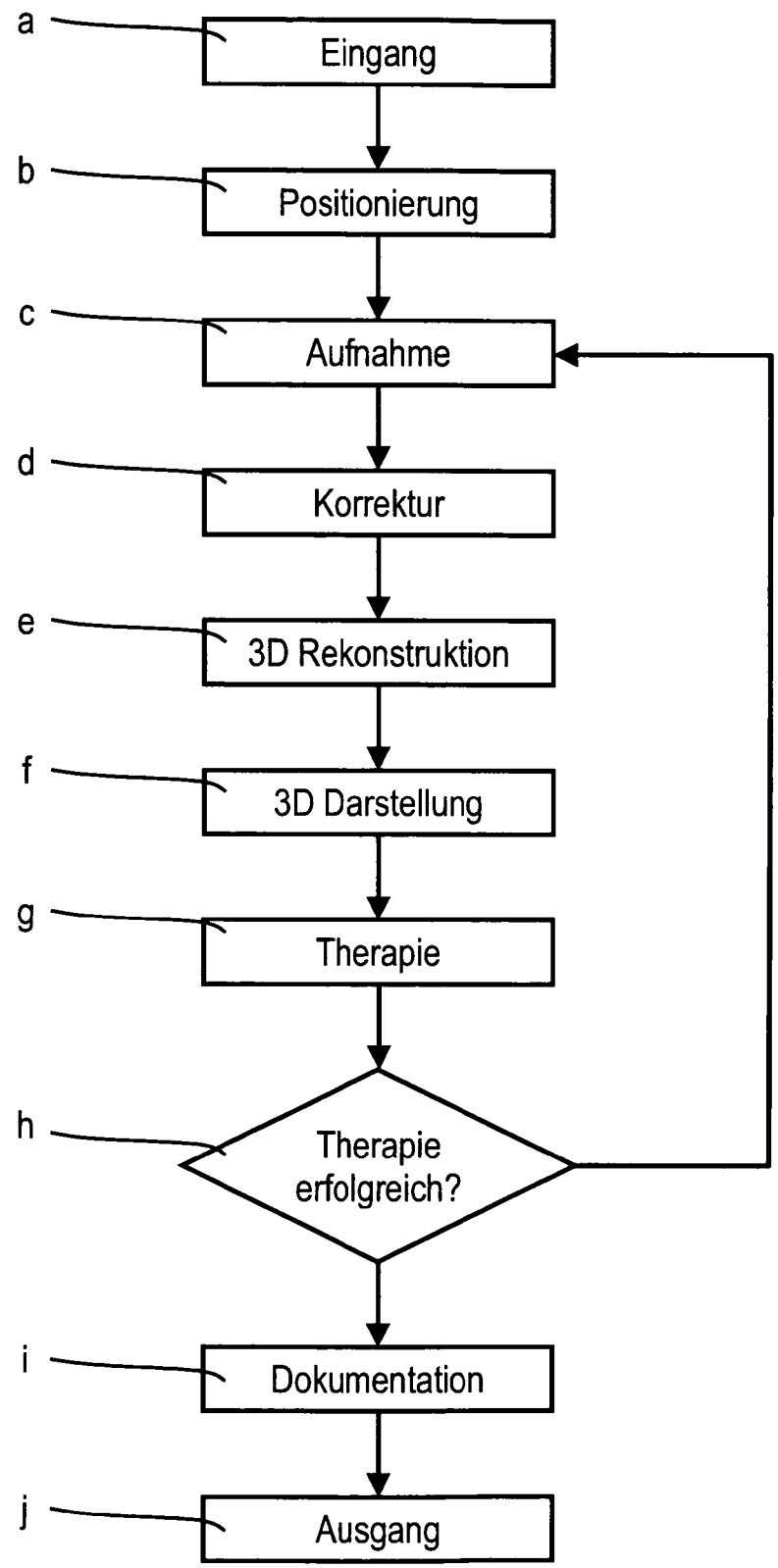

ANGIOGRAPHIC X-RAY DIAGNOSTIC DEVICE FOR ROTATION ANGIOGRAPHY

CROSS REFERENCE TO RELATED APPLICATIONS

This application claims priority to the German application No. 10 2004 057 308.5, filed Nov. 26, 2004 which is incorporated by reference herein in its entirety.

FIELD OF INVENTION

The invention relates to an angiographic x-ray diagnostic device for rotation angiography with an x-ray emitter which can be moved on a circular path around a patient located on a patient support table, with an image detector unit which can be revolved on the circular path facing the x-ray emitter, with a digital image system for recording a plurality of projection images by rotation angiography and with a device for image processing by means of which the projection images are reconstructed into a 3D volume image.

BACKGROUND OF INVENTION

One the most common diseases in the world is vascular disease, such as strokes, aneurysms or the abdominal aortic aneurysms (AAA). A rapid and safe diagnosis and the immediate introduction of treatment are of particular importance for the recovery process of diseases of this type.

The diagnosis of such diseases is supported by imaging methods. In this case, a CT examination is preliminarily carried out in order to precisely determine the extent of the hemorrhaging or of the part of the brain which is no longer supplied with blood. The dimension and form of the vascular deformation is determined in the case of an aneurysm or the AAA. The computer tomograph provides good diagnostic images of the soft tissue in question but CT devices are not able to provide any treatment due to poor patient accessibility. This therapy is generally always carried out with the support of an angiography C-arm x-ray system. The angiographic x-ray systems known to date do not offer an optimum soft tissue resolution and therefore do not allow cerebral hemorrhaging to be viewed for instance.

This results in the patient having to be transferred alley the CT examination into a room in which the angiographic x-ray examination can be carried out. This causes valuable patient treatment time to be lost Concepts in which the computer tomograph and the angiographic x-ray device are accommodated in one shared room offer an improvement. This solution is disadvantageous in that the patient still always has to be relocated and that two relatively expensive devices can be used for just one treatment.

Initial methods and devices for angiographic 3D images using a C-arm x-ray device are known. By way of example, 3D images of a skull and the vessels can be provided using an x-ray diagnostic device with a workstation. DE 102 41 184 A1 discloses a method of this type for generating a volume data set. Further examples for C-arm x-ray devices supplying 3D images are described in Electromedica 1/02 "Initial Clinical Experiences with the SIREMOBIL Iso-C.sup.3D" by Euler et al. on pages 48 to 51 in DE 100 47 364 A1, DE 199 50 793 B4 and DE 103 06 068 A1. As a rule, mobile devices do not radiate sufficient x-ray power and are thus only suited to a limited number of applications. DE 195 09 007 C2 discloses a C-arm x-ray diagnostic device for providing layer images. However, all known C-arm solutions are lacking an optimum display of capillary soft tissue.

SUMMARY OF INVENTION

An object of the invention is to develop an angiographic x-ray diagnostic device for rotation angiography such that the advantages of the angiographic x-ray system are combined with the diagnostic option of improved soft tissue display.

The object is achieved according to the invention with a device for correcting physical effects and/or inadequacies in the recording system for the soft tissue display of projection images and the 3D volume images reconstructed therefrom. As a result of the correction carried out, an angiographic x-ray diagnostic device of this type for rotation angiography still allows a visualization of objects with a difference of 10 Houndsfield Units (KU) and a diameter of 10 mm. In this case the device for correction can be a separate correction processor or a software module in an available correction processor or in the image system of the x-ray diagnostic device.

The method implemented by means of the device according to the invention is similar to the method known for CT systems, however with CT systems, x-ray emitters and x-ray detectors rotate in a closed annular gantry. The use of an open C-arm requires additional image processors and special adjustments and enhancements of the known image processors.

A correction according to the invention can be produced from the group comprising truncation correction, scatter correction, blooming correction, ring artifact correction, correction of the beam hardening and of the low frequency drop.

According to the invention, the device for correction can comprise separate correction process.

Advantageously the device for correction can be embodied such that it effects a calibration of the recording system, for instance a geometry calibration, equalization calibration, intensity calibration and/or gain calibration.

It has proven advantageous for the device for correction to be embodied such that it effects a correction of the movements of the patient and/or the organ movements of the patient.

According to the invention, the x-ray emitter and the image detector unit can be arranged on the respective ends of a C-arm. Alternatively, the C-arm can be mounted on the floor and/or on the ceiling or a mobile C-arm can be used.

Advantageously the x-ray image detector can be a flat, rectangular or square semi-conductor detector, for instance a flat detector (FD), preferably made of aSi.

Two x-ray emitter image detector units which form a dual plane system can also be provided.

BRIEF DESCRIPTION OF THE DRAWINGS

The invention is described in more detail below with reference to an exemplary embodiment illustrated in the drawing, in which:

FIG. 2 shows an examination procedure using the x-ray diagnostic device according to FIG. 1.

DETAILED DESCRIPTION OF INVENTION

Figure 1:
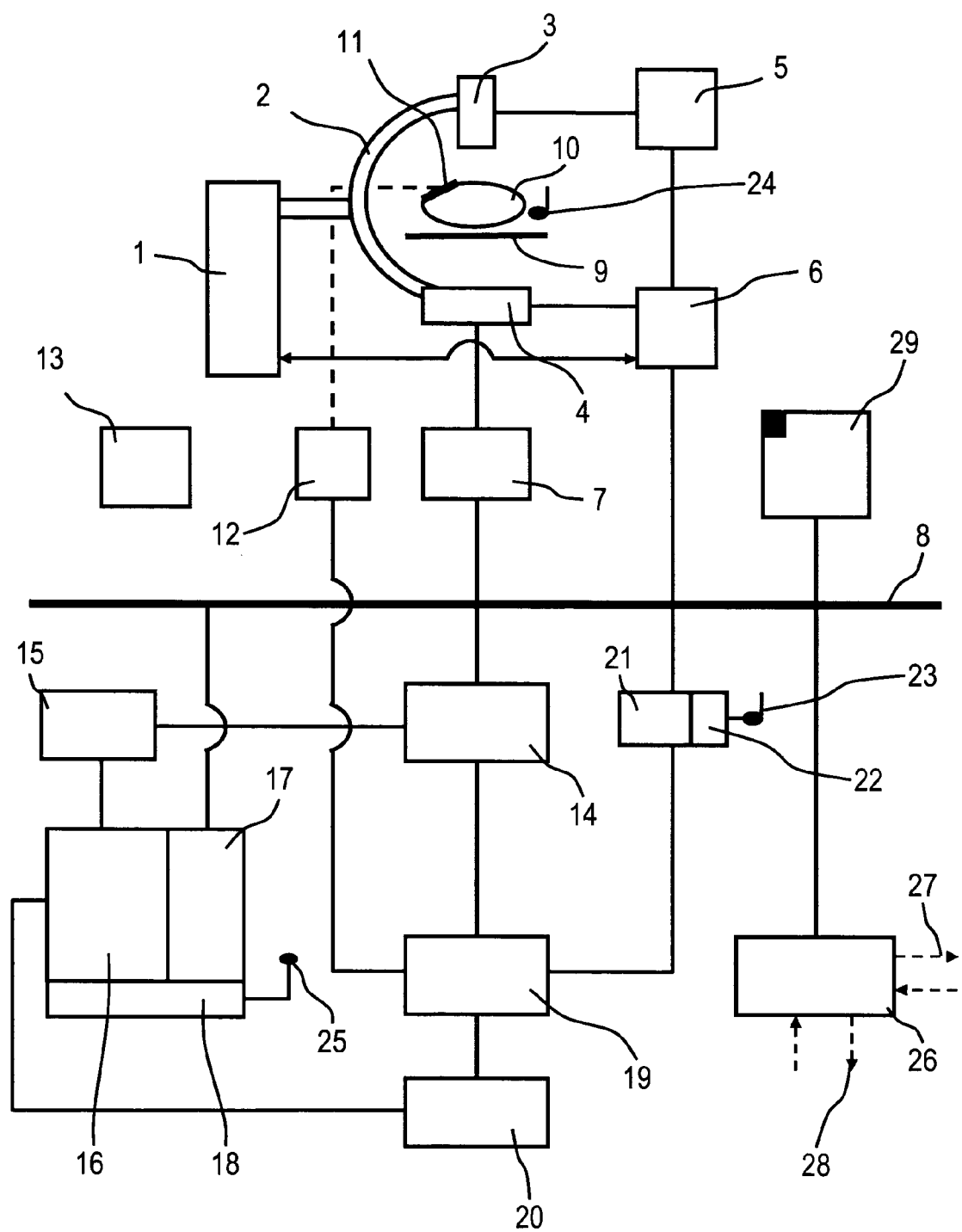
FIG. 1 shows an x-ray diagnostic device according to the invention.

FIG. 1 shows an x-ray diagnostic device comprising a C-arm 2 which is mounted in a rotatable manner on a stand 1, at the end of which is mounted an x-ray emitter 3 and an x-ray image detector 4.

Instead of the support 1 displayed, floor and/or ceiling supports also be used. The C-arm 2 can also be replaced by a so-called electronic C-arm 2, thereby effecting an electronic coupling of the x-ray emitter 3 and x-ray image detector 4, which causes a circular path to be traveled from the x-ray emitter 3 and the x-ray image detector 4, controlled by a computing unit for instance.

The x-ray image detector 4 can be a flat, rectangular and/or square semiconductor detector which is preferably created from amorphous silicon (aSi).

A high voltage generator 5 is connected to a system controller 6 and drives the x-ray emitter 3. The system controller 6 is furthermore connected to the x-ray image detector 4, for instance the aSi flat detector, for the synchronous control of the x-ray emitter 3, when the x-ray image detector 4 is receptive. The system controller 6 similarly controls the motors for rotating the C-arm 2 accommodated in the support 1 for instance and detects the feedback of the position of the C-arm 2.

The image data read out from the x-ray image detector 4 is processed in a pre-processing unit 7 and is supplied to a system data bus 8 for further distribution. The system controller 6 and the pre-processing unit 7 can be part of an image system. Furthermore, they can be implemented as separate hardware or software.

A patient 10 is located on a patient support table 9 in the beam path of the x-ray emitter 3, said patient effecting a damping of the x-ray emission according to their x-ray transparency, said damping being detected by the x-ray image detector 4.

Physiological sensors are attached to the patient 10, said sensors could be ECG electrodes 11 and/or breathing sensors (not shown) for instance. These ECG electrodes 11 are connected to a physiological signal processor 12. A voltage supply unit 13 supplies the individual devices with the voltages they require.

The image data of the signals of the x-ray image detector 4 processed by the pre-processing unit 7 are supplied to an image processing unit 14 for x-ray images. On the one hand, this is linked to a 2D-3D display unit 16 by way of a 2D processing 15. Together with an input unit 17 (USER I/O) and a 3D display controller 8, this 2D-3D display unit 16 forms a playback unit.

A receiver 25 for a sensor for head movements can be linked to the 3D display controller 18 in order to adjust the 3D display to head movements of the doctor examining and observing the 2D-3D display unit.

The image processing unit 14 is further connected to a correction unit 19 for image artifacts and images. The output signals of this correction unit 19 are supplied to the 2D-3D display unit 16 for three-dimensional playback via a 3D image reconstruction 20.

A calibration unit 21 and a position sensor interface 22 are also connected to the system data bus 8, said position sensor interface 22 being connected to a receiver 23 for signals outgoing from a sensor for patient movement. The sensor 24 can detect movements of the patient lying on the patient support table by means of electromagnetic waves, such as ultrasound for example; and reports these to the receiver 23 by means of radio waves for instance.

A DICOM interface 26 is connected to the system data bus 8 for outward communication purposes, said DICOM interface exchanging patient data via data lines with the HIS 27 and exchanging image data via further data lines 28 by means of the hospitals' intranet or via the internet. The DICOM interface 26 can feature the MPPS function (Modality Performed Procedure Step).

Furthermore, an image data memory 29 is connected to the system data bus 8, which brings about an intermediate storage of the image data supplied by the pre-processing unit 7, so that it is subsequently called up by the image processing unit 14 and/or can be routed via the DICOM interface 26.

All processors can be implemented as separate hardware or software and integrated into the image system.

An angiographic x-ray diagnostics device is thus provided, comprising at least one C-arm 2 which is mounted in, a rotatable manner, at which ends are accommodated an x-ray emitter 3 with a radiation diaphragm and an x-ray image detector unit 4, a high voltage generator 5, a patient support table 9, radiation and detector stands 1 and an image processing unit 14. In additions image processing processors 20 are used which allow a plurality of projection images to be recorded by means of rotation angiography. These projection images are reconstructed into a 3D volume image with the aid of the image processing processors 20.

In accordance with the inventions image artifact processors and correction processors are provided, which allow a good soft tissue display of projection images and the 3D volume images reconstructed therefrom. At the same time, the previous preferences of the angiographic x-ray diagnostic device are retained, such as a good detail resolution and accessibility to the patient.

The C-arms 2 with x-ray emitter 3 and x-ray image detector 4 move in this case preferably through an angular range of at least 180°, for instance 180° plus fan angle, and record projection images from different projections in quick succession. The reconstruction can only take place from one subarea of this recorded data.

In this case, the device comprising a C-arm 2, x-ray emitter 3 and x-ray image detector 4 can be mounted on the floor or the ceiling. Alternately a mobile C-arm can be used for specific applications.

The x-ray image detector 4 is preferably an aSi flat detector.

For 3D reconstruction, two-dimensional (2D) cone beam projections of a three-dimensional (3D) object are recorded by the C-arm device 2 to 4 during a partial circular orbit. The underlying 3D object function from this set of 2D projections can be calculated or estimated using the Feldkamp algorithm for instance, which is described in "Practical cone-beam reconstruction," by L. A. Feldkamp, L. C. Davis, and J. W. Kress, in J. Opt. Soc. Am. A, Vol. 1, No. 6, pages 612-619, 1984. This method, which relates to the principle "filtered back projection" allows one layer at most to be mathematically precisely calculated, namely that which lies in the circular path orbit, the center plan. Layers lying outside the center plane can only be calculated approximately. This means that not all data can be collected during a circular path orbit, which is required to accurately calculate layers outside the center plane. Despite this restriction, the Feldkamp algorithm currently offers an attractive compromise between computational costs and result. From a mathematical point of view, more precise results can be achieved using exact 3D reconstruction methods. In this case, efficient and exact 3D reconstruction methods relating similarly to filtered back projections, as known for instance from "A general scheme for constructing inversion algorithms for cone beam CT," by A. Katsevich, from Int. J. Math. Math. Sci. 21, pages 1305-1321, 2003, are particularly interesting.

The 3D image reconstruction is carried out for instance with the Feldkamp algorithm. Other algorithms for the reconstruction can likewise be used, e.g. the 3D Radon Inversion (Grangeat's Algorithm), the Defrise-Clack Filtered Back Projection, Fourier methods or iterative methods such as are described for example in "Mathematical Methods in Image Reconstruction", by F. Natterer und F. Wübbeling in Society for Industrial and Applied Mathematics, Philadelphia 2001.

In this case however, the non-ideal focus and detector path trajectories also have to be considered. A reconstruction method which also includes non-ideal C-arm geometry and the partial circular path orbit is described by K. Wiesent et al. in "Enhanced 3-D Reconstruction Algorithm for C-Arm Systems Suitable for Interventional Procedures", IEEE Trans. Med. Imag., Vol. 19, No. 5, 2000. Alternatively, other analytical cone beam methods, algebraic and/or statistical reconstruction methods can be used.

The artifact and correction processors comprise a number of subprocessors which can consist of hardware, software or a combination of hardware and software. The respective processors can be individually disconnected. The sequence with which these corrections are carried out can be selected and configured in its parameters, so that different types of examination with different parameters can be stored and can be activated by inputting the name of the examination, e.g. 'stroke' and the complete x-ray systems including the image processing and image/data distribution is parameterized and initialized via the network.

The following artifact and correction processors are used as the correction unit 19 for image artifacts and images.

Processors for Calibrating the Recording System

The calibration of the recording system to be carried out at the beginning comprises a number of parts:

Geometry Calibration:

Geometry calibration allows the x-ray optical characteristics, i.e. the position of the x-ray focus and the position and orientation of the x-ray image detector 4 to be determined for every projection. This is important in order to be able to achieve reconstructions with high spatial resolution and free of artifacts, since a C-arm x-ray system can exhibit deviations from the ideal circular path due to instabilities.

Equalizations Only for X-Ray Image Amplifiers, not Necessary for Flat Screen Detectors:

The projection images of the x-ray image amplifier comprise distortions arising in part from the earth's magnetic field and in part from inadequacies of the electron optical characteristics. These distortions are eliminated in a correction procedure.

Intensity Calibration:

Intensity calibration allows an intensity I and (after determination of the intensity $I_0$ without object) a line integral $p=\ln(I_0/I)$ to be assigned to each grey value in the projection image. These line integrals are the input for the respective reconstruction algorithm.

Gain Calibration:

A gain calibration of the x-ray image detector 4 is achieved with the aid of a so-called 'Flat Field Image'. This gain calibration is important in order to suppress Fixed Pattern Noise which brings about artifacts in the reconstructed image (e.g. Ring Artifact). For this purpose, each measured projection is corrected using the 'Flat Field Image'.

Truncation Correction

Every practical x-ray recording device has an x-ray image detector of finite size. Objects whose projection exceeds the dimensions of the x-ray image detector can thus no longer be completely detected and so-called segmented projections result. An exact reconstruction of a 3D object function made from segmented projections is generally not possible, even if, in principle, the underlying algorithms allow this with completely recorded projections. Extrapolation methods are known, with which the quality of a reconstructed 3D volume can be improved, such as that described for instance by B. Ohnesorge, T. Flohr, K. Schwarz, J. P. Heiken, and K. T. Bae in "Efficient correction for CT image artifacts caused by objects extending outside the scan field of view," Med Phys, vol. 1, pages 39-46, 2000. If more precise solutions are sought, reference is usually made to a-priori-Information, e.g. a CT-data set, see (K. Ramamurthi, J. L. Prince, "Tomographic Reconstruction for Truncated Cone Beam Data Using Prior CT Information," MICCAI (2), 134-141, 2003).

Scatter Correction

In contrast to radiography, scatter with CT reconstruction not only results in a deterioration of the signal/noise ratio, but also in object-dependent grey value corruption such as 'cupping' as well as beam artifacts or shadow artifacts, which can significantly impair both the quantitative precision and also the detectability of low contrasts.

In conventional CT devices with detector arrays comprising one or more lines, the scatter can be reduced by means of slotted collimators to such an extent that it practically no longer effects the image. In the case of a CT with a surface detector, the completely penetrated body cross-section functions as a scatter source, with the intensity of the scatter reaching the flat panel detector even able to exceed the unweakened primary radiation. The use of a scatter grid can thus selectively reduce the fraction of the scatter, but still affects the image and is thus not negligible (Scatter-Fraction approx. 25% with cranial images, up to more than 50% with thorax, pelvic or abdominal images).

Scatter correction methods comprise two components, a method for estimating the scatter distribution at the detector level and a correction algorithm. In order to estimate the scatter, a measuring method with the known beam stop methods has been proposed by R. Ning, X. Tang, D. L. Conover. in "X-ray scatter suppression algorithm for cone beam volume CT". Proc. SPIE, Vol. 4682, 2002, pages 774-781, said method however rarely recommended for the clinical workflow due to reasons of manageability. Other methods are based on computer models which can be adapted with sufficient precision to measurements and/or Monte Carlo simulation calculations and result in significant image improvements. Computer models exists which operate directly on projection images and are known for instance from U.S. Pat. No. 5,666,391, or iterative methods which also allow the use of information from the volume reconstruction are described in the German patent application 10 2004 029 009.1.

Blooming Correction

The bit depth of the x-ray image detectors used with C-arm systems is currently relatively small in comparison with modern CT detectors (12 bit for CCD camera and 14 bit for flat detectors in comparison with 18 to 20 bit with CT-detectors). Thus blooming radiation often results in projections, which in turn result in artifacts in the reconstruction. These blooming radiation artifacts can be reduced by extrapolating the projection values whilst avoiding the clipping.

Low Frequency Drop

Scattered light in the x-ray image detector gives rise to a background in the projection images, which mathematically corresponds to a convulsion with a point spread function. This background results in artifacts in the reconstructed image (similar to scatter) and can be corrected by a corresponding deconvolution of the projection data.

Ring Artifact Correction

Even with careful calibration of the x-ray image detector 4 the measurement data contain individual detector pixels, measurement results and fluctuations. These errors result in ring artifacts in the reconstructed images. The use of suitable (radially and circularly effective) filters allows a ring image to be separated from the object image. The ring structure is first detected preferably by median filtration of the original image and subsequently by subtraction. Other radial smoothing filtration can similarly also be used. A smoothing of this image in a circular direction causes the noise proportion contained therein to be eliminated. The ring image achieved in this way is subsequently subtracted from the original image.

Correction of the Beam Hardening

The hardening of the x-ray on penetration of an absorbent object according to H. Barrett, W. Swindell in Radiological Imaging, Vol. 2, Chap. 7, causes the image element in axial images to be reconstructed at the image center with minimum grey values. This so-called key effect prevents a homogenous image impression. The key effect is avoided if the projection data is calculated on an imaginary monoenergetic x-ray. This conversion takes place for soft tissue in a pre-reconstructive step and for more dense objects such as bones and metal in a post-reconstructive step with subsequent second image reconstruction.

Processor for Movement Correction of Patient Movements

This solution can be based on the calculation of the movement from the 2D images available or the movement can be determined via a movement detector attached to the patient and used for image correction purposes. U.S. Pat. No. 6,233,476 and US 2001/0031919 disclose movement detectors for compensating patient movements in conjunction with the electromagnetic positioning of medical instruments. The movement detector 24 attached to the patient is preferably implemented wirelessly, e.g. with 'Bluetooth'.

Correction of Organ Movements by the Beating Heart ("ECG-Gating")

For this purpose the ECG of the patient is prerecorded and supplied to the correction unit of the image system. The corresponding correction algorithms allow movement artifacts to be calculated from the image reconstruction.

Processor for Eliminating Movement Artifacts Effected by Breathing

A chest band can be used to eliminate the breathing artifacts, said chest band determining the breathing amplitude and the frequency by means of corresponding sensors and introducing correction calculations in the image processing unit which deduces the movement artifacts from the image information. Alternatively, the amplitude and the frequency can be calculated from the envelope of the ECO signal and supplied to the correction unit 19 of the image processing unit. The movement artifacts can be deduced from the image reconstruction by means of corresponding calculations.

The examination procedure by means of the angiographic x-ray diagnostics device according to the invention comprises the following steps a through j illustrated in FIG. 2.

Input:

Check-in, identify and register the patient, either manually or via a data interface, e.g. DICOM.

Positioning:

Support and position the patient on the examination table

Record:

Record a rotation angiography of at least 180° with at least two projection images (an increase in the number of projections and of the angular range improves the image quality)

Correction:

Artifact correction by means of the correction processors according to the invention 3D Reconstruction:

Reconstruction of the 3D volume image

3D Display:

Display the 3D volume image on a display or projection device.

Treatment:

Implement the treatment measures, preferably minimally invasive

Treatment Successful?:

Check the treatment measures by repeating steps c) to f)

Documentation:

Document the diagnosis and treatment on an integrated computing unit

Output:

Release the patient, dispatch and archive the documented diagnosis and treatment data, preferably via a medical data network (e.g. DICOM-MPPS).

An alternative embodiment for applications with reduced requirements regarding the resolution is proposed, in that the x-ray images are generated using methods of the discrete tomography made from few projections, particularly after a first 3D image data set was generated with high resolution. A method for discrete tomography is described for instance in DE 102 24 011 A1. This is advantageous in that the patient and the clinician are only subjected to a minimal radiation exposure.

These images can also be supported by administering contrast means. Optionally the images can be recorded in DSA mode or without DSA.

The image system contains a 3D display for displaying 3D photos, preferably a flat screen. This solution allows the three-dimensional examination without auxiliary means such as 3D glasses for instance.

In addition, the observer can wear a head band or a normal pair of glasses with positional sensors, so that the line of sight of the observer is synchronized with the observation direction of the 3D object via corresponding processors. An example for the determination of the line of sight of an observer and the tracking of an image object is described in U.S. Pat. No. 5,646,525.

Alternatively or in addition, the 2D and/or 3D photos can be projected by means of a projection device ('beamer') in 2D or 3D display onto a projection surface, for instance a wall of the examination room, as described in DE 100 36 143 C2.

The examination device contains a DICOM-Interface 26 including MPPS (Modality Performed Procedure Step), which can process all image information and patient data.

Besides normal 2D x-ray examinations, the device allows 3D reconstructions.

It is advantageous to equip the patient support table 9 with an x-ray transparent table plate and with at least one of the following properties:

Longitudinal tilting,

Motor support of all movements,

Ability to tilt up to 90°,

Lateral tilt,

Fastening rails for accessories. The accessories can be at least one of the systems mentioned.

It is worthwhile integrating a contrast means injector such as that made by Medrad and Tyco Healthcare for instance.

Furthermore, a patient monitoring system for monitoring the vital functions of a patient can be integrated. Thus an alarm can be triggered if specific vital parameter boundaries of a patient are exceeded or not met. A subsystem for applying anesthetic can be added, e.g. an anesthetic ventilator.

The proposed solution is advantageous in that the diagnosis and treatments implemented nowadays using a number of medical devices can be implemented with one single system in a significantly more secure and rapid manner. This solution enables the planning, guidance and control of the treatment using just one device.

Instead of a flat detector as an x-ray image detector 4, an x-ray image amplifier can also be used with a coupled CCD camera. The rotation angiography according to the invention is however far more difficult to implement, since a circular image is generated with the x-ray image amplifier, said image additionally comprising distortions at the circular image edge on the basis of geometrical distortions at the x-ray image amplifier. This would require an adjustment of the algorithms to the image construction and requires an additional distortion correction.

The device according to the invention improves the diagnostic possibilities of an angiographic examination by applying the angiographic computer tomography (ACT) using an angiographic x-ray diagnostic device. Thus CT-similar images can be generated during an angiographic procedure.

Neurovascular treatments always run the risk of complications. Local hemorrhaging as a result of aneurismal ruptures can be visualized with angiographic examinations by means of the device according to the invention. Furthermore, the ventricular system of the brain can be displayed to support the diagnosis of pathological processes. The guidance and observation of placements is also enabled during drainage procedures.

The device according to the invention enables an exceptional diagnostic with abdominal procedures and interventional support also with punctures and drainages.

For oncological applications, the device according to the invention allows the visualization of tumors within all body parts, thereby allowing completely new methods for implementing biopsies or treating tumors to be realized, such as embolisms or ablations for instance.

The invention claimed is:

1. An angiographic x-ray diagnostic device providing rotation angiography for performing an angiographic treatment procedure on a patient and for generating diagnostic images of soft tissue at sufficient resolution for diagnosis as to render unnecessary separate generation of a CT examination, the device comprising:
    an open C-arm
    an x-ray emitter mounted on the C-arm and configured to be moved along a circular path around a patient located on a patient support table;
    an image detector unit mounted on the C-arm and configured to be moved along the circular path, the image detector facing the x-ray emitter;
    a digital image system for recording a plurality of projection images by rotation angiography;
    an image processing unit for reconstructing a three-dimensional volume image from the projection images, wherein the combination of the open C-arm, the x-ray emitter, the image detector unit, the digital image system and the image processing unit collectively provide an angiographic x-ray imaging function to enable provision of the angiographic treatment procedure; and
    a correction unit connected to the digital image system for correcting unwanted physical effects or inadequacies related to the digital image system, the correction unit configured to enhance recording of soft tissue such that an image quality of the projection images recorded from the soft tissue and the corresponding three-dimensional volume image is improved;
    wherein the correction unit is configured to execute a correction method chosen from the group consisting of a truncation correction, a scatter correction, a blooming correction, a ring artifact correction, a correction of movements of the patient, and a correction of organ movements of the patient such that with operation of the correction unit the image processing unit provides diagnostic images of soft tissue with sufficient resolution, relative to that achievable with a CT system of the type in which an x-ray emitter and an x-ray detector rotate in a closed annular gantry, that examination with such a CT system is not needed to perform the diagnosis as needed for the angiographic treatment procedure.

2. The angiographic x-ray diagnostic device according to claim 1, wherein the correction unit comprises a separate correction processor specialized in executing a correction method.

3. The angiographic x-ray diagnostic device according to claim 1, wherein the correction unit is configured to execute a calibration of the digital image system.

4. The angiographic x-ray diagnostic device according to claim 3, wherein the calibration is a geometry calibration, a distortion calibration, an intensity calibration or a gain calibration.

5. The angiographic x-ray diagnostic device according to claim 1, wherein the x-ray emitter and the image detector unit are arranged on opposite ends of the C-arm.

6. The angiographic x-ray diagnostic device according to claim 5, wherein the C-arm is mounted in a rotatable manner.

7. The angiographic x-ray diagnostic device according to claim 1, wherein the x-ray image detector is a flat rectangular or flat quadratic semi-conductor detector.

8. The angiographic x-ray diagnostic device according to claim 7, wherein the x-ray image detector is based on aSi.

9. The angiographic x-ray diagnostic device according to claim 1, comprising one image detector unit and one x-ray emitter.

10. The angiographic x-ray diagnostic device of claim 1 wherein, with operation of the correction unit, the image processing unit provides a diagnostic image of capillary soft tissue with sufficient resolution, relative to that achievable with a CT system of the type in which an x-ray emitter and an x-ray detector rotate in a closed annular gantry, that examination the capillary soft tissue with such a CT system is not needed to perform the diagnosis.

11. The angiographic x-ray diagnostic device according to claim 1, wherein the angiographic x-ray diagnostic device includes only one C-arm and only one image detector unit and only one x-ray emitter are attached to the C-arm.

* * * * *